United States Patent [19]

Schwartz et al.

[11] 4,260,842
[45] Apr. 7, 1981

[54] ISOMERIZATION OF OLEFINS UTILIZING HETEROGENEOUS DIOXYZIRCONIUM CATALYSTS

[75] Inventors: Jeffrey Schwartz; Michael D. Ward, both of Princeton, N.J.

[73] Assignee: The Trustees of Princeton University, Princeton, N.J.

[21] Appl. No.: 91,963

[22] Filed: Nov. 7, 1979

[51] Int. Cl.³ .......................... C07C 5/22; C07C 5/23; C07C 5/25
[52] U.S. Cl. .................................. 585/377; 585/477; 585/664; 585/671; 252/461
[58] Field of Search ............... 585/377, 477, 664, 671; 252/461

[56] References Cited

U.S. PATENT DOCUMENTS

| | | | |
|---|---|---|---|
| 3,671,597 | 6/1972 | Kroll | 585/363 |
| 4,125,567 | 11/1978 | Kidwell et al. | 585/371 |

OTHER PUBLICATIONS

Chem. Ab. 77:87709z, 1972 [G. V. Lisichkin et al. Zh. Fiz. Khim. 46(4), 1056–1057, 1972 (Russ.)].
Chem. Ab. 88:7475j, 1978 [V. A. Zakharov, J. Mol. Catal. 2(6) 421–435, 1977 (Eng)].

*Primary Examiner*—Veronica O'Keefe
*Attorney, Agent, or Firm*—Omri M. Behr

[57] ABSTRACT

It has been found that catalysts comprising zirconium hydrides, hydride alkyls and dihydrides bonded to metal or metalloid oxides in particular zirconium hydride bonded to silica, when contacted with olefins under mild conditions rapidly cause isomerization to thermodynamic mixtures.

7 Claims, 3 Drawing Figures

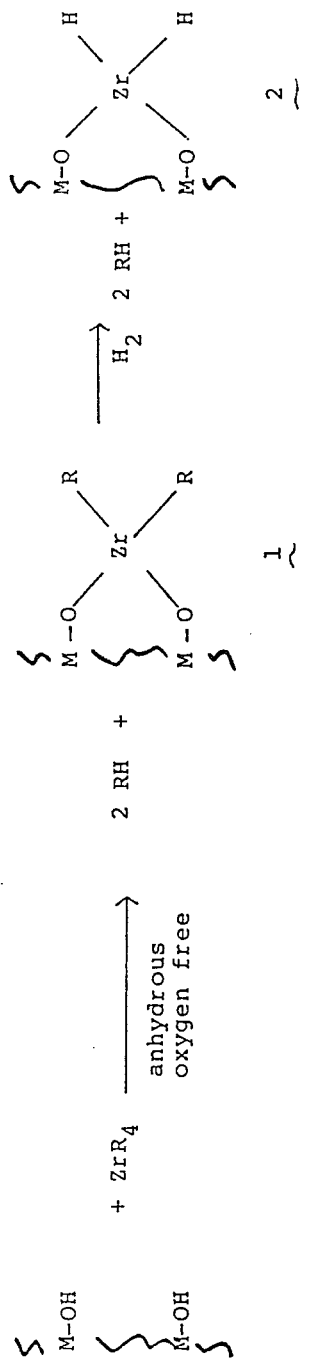
FIGURE I

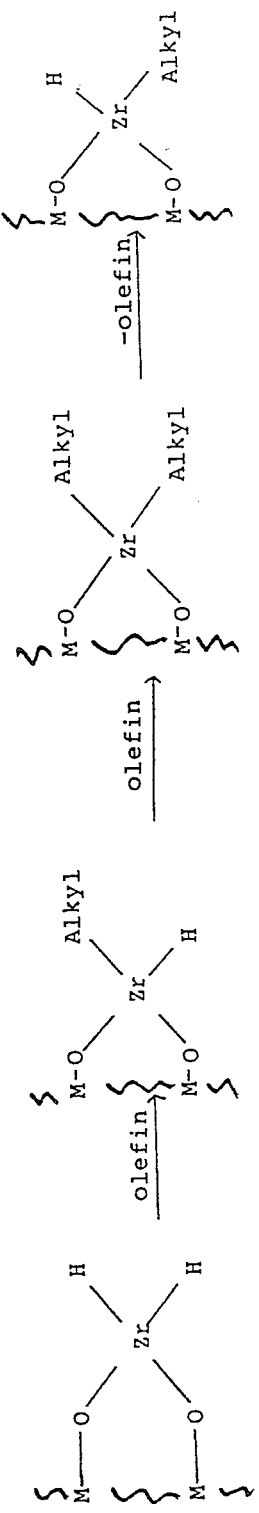
FIGURE II
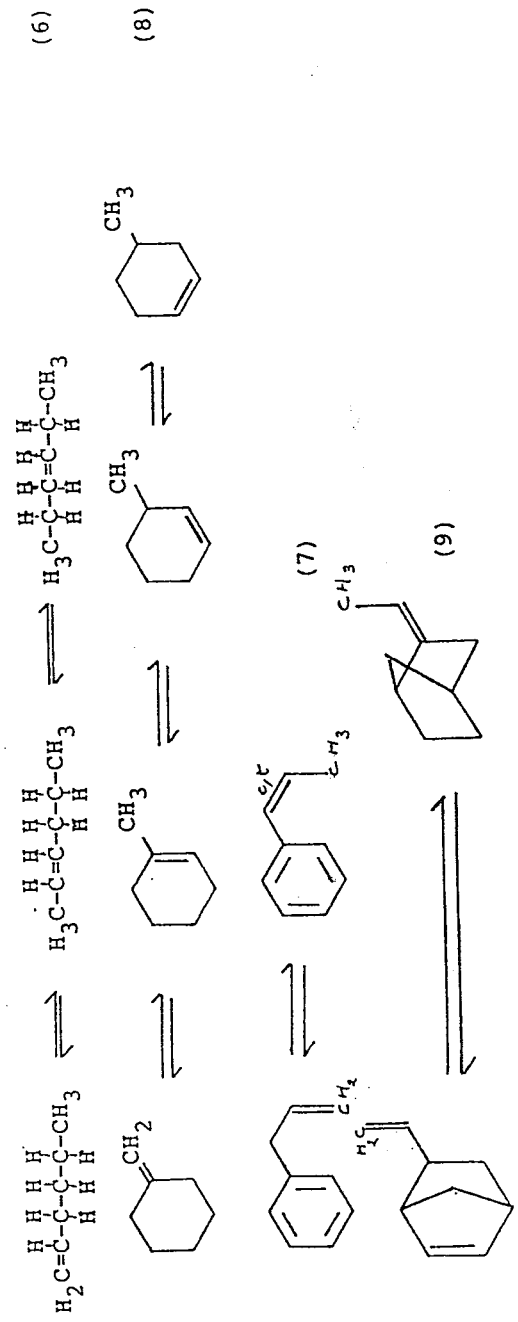
FIGURE III

ISOMERIZATION OF OLEFINS UTILIZING HETEROGENEOUS DIOXYZIRCONIUM CATALYSTS

BACKGROUND OF THE INVENTION

Olefins, in particular, monounsaturated olefins and nonconjugated polyunsaturated olefins which may be straight chain, branch chain, cyclic, or a combination thereof, are often produced relatively readily as isomers which are not the most valuable isomers in commercial or industrial usage. The conversion of these isomers to provide at least the thermodynamic mixture of the theoretically available isomers wherein the double bond or double bonds are in different positions has therefore been a desirable goal.

Among the previously reported approaches to solution of this problem may be mentioned U.S. Pat. No. 3,671,597 to Kroll. Kroll utilizes group VIII transition metals absorbed on certain metal oxide or metaloid oxide carriers to effect isomerization of terminal aliphatic olefins. The range of temperature at which the isomerizations are carried out are disclosed as lying between 100 and 200 degrees C.

Lisichkin, et al (Zh. Fiz. Khim. 1972, 46, 1056) report that certain "hydrides" specifically Ti, Zr, Hf, $TiH_2$, $ZrH_2$, and $HfH_2$ will convert 1-hexene to 2-hexene and 3-hexene. This work indicates that in the case of zirconium and hafnium there is substantially no isomerization below 350 degrees and in the case of titanium a graph indicates a 30% isomerization at about 200 degrees rising to a peak of about 70% at about 350 degrees. Full evaluation of the significance of Lisichkin's work is difficult since titanium, zirconium and hafnium are known to be tetra valent and the exact meaning of the "hydrides" discussed in the paper is therefore not clear. Furthermore, there is no disclosure as to how the "hydrides" are prepared or how the 1-hexene is contacted with the catalyst.

In a related area, U.S. Pat. No. 4,125,567 to Kidwell and Lynch discuss the use of dicyclopentadienyl metal alkyls which cause the conversion of internal olefins to terminal olefins, a somewhat more specific aim than is intended by the present invention. It should also be noted that the catalyst organometallic reagent utilized by Kidwell is not a supported catalyst and therefore its separation from the reaction mixture is somewhat more cumbersome than would be the case in the use of supported catalysts.

The preparation of zirconium alkyls supported on a silica carrier as well zirconium hydrides similarly supported are disclosed by Zakharov, et al (J. Mol Cat. 2, 421, 1977) catalysts of this type are disclosed as being valuable for ethylene polymerization. There is no discussion by Zakharov, et al of any isomerization reactions although they do indicate (at page 431) and at page 434 that a bond between the zirconium and an olefin moiety does form and they further disclose that the thus coupled olefin moiety may be removed by the action of hydrogen to provide the corresponding supported zirconium hydride and the corresponding alkane. Methods for the formation of the aforementioned zirconium hydride silica supported catalysts may also be found in a paper by Candlin and Thomas (Adv. Chem. Ser., 132 212, 1974). Candlin and Thomas are concerned with polymerization and disproportionation and their work is not directed to isomerization.

SUMMARY OF THE INVENTION

There is provided a process for the isomerization of olefins, for example monounsaturated olefins as well as polyunsaturated olefins containing at least one nonconjugated double bond, which may be straight chain or branched chain, and may include cyclic moieties suitably carrying at least one ring substituent to localize the position of double bond wherein the double bond or double bonds may be inside the ring, on the side chain, or both and may further include aromatic compounds having a nonconjugated alkenyl side chain and which may, additionally, be fused with or bonded via a carbon carbon bond to other aromatic rings or alicyclic rings which may, if desired, also have nonconjugated double bonds therein.

The catalyst (2, 3, 3', or 4) utilized comprises a zirconium moiety bonded to a metal or metalloic oxide support phase wherein [M.oxide] is the oxide of a group II, group III, group IV, group V or group VIB metal suitably group IIA, group IIIA, or group VB most suitably group IIIA as well as the oxide of the metalloid silicon. In the moiety $R_1$ and $R_2$ may be hydrogen or alkyl and may be the same or different. In particular, but this is in no way to be considered a critical limitation, the alkyl moiety $R_1$ or $R_2$ or both may be the alkyl derived from the olefin to be isomerized for example where the olefin is a butene $R_1$ or $R_2$ would be butyl, where the olefin is allylbenzene $R_1$ or $R_2$ would be 1-phenylpropyl.

The reaction is carried out heterogenously. The heterogenous components are the solid catalysts, the olefin and, if desired, a solvent. The presence of a solvent is not critical. The reaction may be carried out in gas/solid phases. Where the olefin is, at the temperature reaction, a liquid then the reaction may be carried out in the liquid/solid phase. Where a solvent is present, the actual isomerization reaction probably takes place between that portion of the gaseous phase olefin dissolved in the solvent and the catalyst. The invention however is not to be considered limited by this hypothesis.

The isomerization will occur at very moderate temperatures. It has been found that in the case of straight or branched chain olefins, the reaction will take place readily and rapidly at ambient temperature. However, where the olefin is or contains cyclic components slightly more elevated temperatures suitably 20 to 30 degrees above ambient temperature are desirable to provide a satisfactory rate of reaction.

BRIEF DESCRIPTION OF THE DRAWINGS

FIG. I is a flow sequence showing formation of a dihydrozirconyl moiety on a metal oxide.

FIG. II is a flow sequence of the interaction of the product of FIG. I with an olefin.

FIG. III illustrates possible isomerization sequences.

DESCRIPTION OF THE PREFERRED EMBODIMENTS

In the process of the present invention aliphatic and cyclic mono olefins, diolefins, and polyolefins are isomerized to the corresponding thermodynamic mixture by contacting a feed containing said olefins with a heterogeneous catalyst comprising a solid support phase of metal or metalloid oxide bonded to zirconium hydride, alkyl hydride, or dialkyl.

The olefins which may be isomerized by the process of the present invention include aliphatic olefins which may be straight chain olefins of at least four carbon atoms, or branched chain olefins of at least five carbon atoms. Where longer chains are to be isomerized, more than one double bond may be present provided that in the feed stock at least two double bonds are not conjugated with respect to each other. While the feed olefin will generally be a terminal olefin the invention is in no way to be considered as limited thereto.

The cyclic mono, di, or polyolefins considered to be suitable feed materials within the scope of the present invention fall into several additional categories. There are included monocycloalkenes suitably having four to eight carbon atoms in a single ring. Such compounds will generally speaking have at least one substituent on the ring in order to define the position of the double bond. There are also included polycycloalkenes that is to say compounds comprising a system of mutually fused rings or mutually bonded rings, said rings having between four and nine members in each ring system although the invention is not limited to these ring numbers. Said ring systems are non-aromatic, carbocyclic ring systems containing at least one double bond in at least one ring moiety and where more than one double bond is present at least two of the double bonds are not mutually conjugated. Included in such systems are, for example, octahydronaphthalene, cyclohexylcyclohexene, and (2.2.1) bicycloheptenes. Also included are cyclopolyalkenes of suitably of six to ten carbon atoms in the ring. For example, 1,4-cyclohexadiene 1,5-cycloheptadiene and 1-cyclopentyl-1,4-cyclohexadiene.

Also included are polycyclopolyalkenes of at least 6 carbon atoms in the ring wherein the rings of the system may be fused to each other or connected by one or more carbon-carbon bonds or at least one double bond is not conjugated with for example 5-alkenylbicycloheptenes for example vinyl bicyclo [2.2.1] hept-2-ene otherwise known as vinyl norbornene, 5-propenylbicyclo [2.2.1] hept-2-ene and the like.

Further there may be included alkenyl cycloalkanes for example vinylcyclohexane or allycycloheptane, or alkenyl polycycloalkanes such as vinyl decalin or allyldecahydroanthracene and the like said cycloalkenes or cycloalkanes having at least four carbon atoms in each ring moiety.

Also included within the scope of the present invention as feed materials are alkenyl carbocyclic aromatic compounds, wherein said alkenyl moiety has at least three carbon atoms and at least one double bond in the system is either not mutually conjugated with another nonaromatic double bond or with the said aromatic group, said aromatic group being selected from the group consisting of those having a monocyclic nucleus for example benzene or a monocyclic aromatic nucleus fused to or bonded to at least one other aromatic nucleus, suitably naphthalene, anthracene, fluorene, biphenylene or the like as well as cyclic aromatic systems fused to alicyclic moieties for example indane, acenaphthene, dihydro- and tetrahydro naphthalene, and the like.

The catalyst comprises a support phase consisting of a metal or metalloid oxide having bonded thereto. The catalyst moiety which may be generally represented by the formula

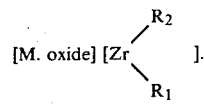

In the foregoing formula M is a metal of Group II, Group III, Group IV, Group V and Group VI B of the periodic chart of elements. Preferably [M. oxide] represents the oxide of a Group II, Group III A or Group IV B metal for example zinc oxide, magnesia, calcium oxide, strontium oxide, barium oxide, titania, zirconia or vanadia. Especially preferred among the metal oxides are the group III A metal oxides, boria and alumina also within the scope of the invention are metalloid oxides such as silica and germania. The support phases should not be considered as limited to single compounds. It should be noted that combinations of the foregoing support phases, for example silica/alumina, are effective and fall within the preferred category.

The zirconium moiety has two of its available valence bonds attached to two oxygens of the support phase. The other two bonds may both be attached to hydrogens to form the dihydride 2 or to alkyl groups to form the dialkyl 4 or to one hydrogen and one alkyl to form the alkyl hydride 3 or 3'. It should be noted, however, as will be seen by the form the reaction scheme set forth in FIG. II that in the operation of the isomerization reaction an equilibrium between these three embodiments comes to exist. The equilibrium existing between the dialkyl and the alkyl hydride 3 or 3' forms depends, however, upon the elimination of a beta hydrogen upon an alkyl moiety. Therefore, while some isomerization will occur when the B-hydrogen is absent, for efficient operation of the system, the alkyl moiety attached to the zirconium atom shall contain at least one beta hydrogen.

Since the stability of zirconium tetraalkyls devoid of beta hydrogen atoms is substantially greater than the stability of zirconium tetraalkyls having a beta hydrogen it has been found convenient to prepare, as is taught by the prior art, zirconium tetraalkyls devoid of a beta hydrogen in the alkyl moiety, for example tetraallyzirconium or tetraneopentylzirconium which are then reacted with the support phase oxide. Due to steric considerations, statistically speaking, only two of the alkyls on the tetraalkyl zirconium moiety react with the support phase oxide provide a dioxyzirconium dialkyl[(1)] which is then hydrogenated to provide the dihydride embodiment[(2)]. If desired, this dihydride can then be reacted with one or two equivalents of a pre-determined olefin to provide the corresponding mono or di adduct, namely the corresponding dioxyzirconium alkyl hydride[(3)] dioxyzirconium dialkyl compound.

From a practical point of view, however, there is no reason to carry out this reaction which will, in any event, occur during the isomerization process when the catalyst is contacted with the olefin to be isomerized. For this reason therefore it is preferred to carry out the isomerization using the dioxyzirconium dihydride compound.

In the preferred mode of preparation of the dihydride compound,[(2)] the support phase, suitably silica or alumina, is heated at elevated temperatures under reduced pressure. Temperatures of the order of 180° to 400° C., at pressures of between $10^{-3}$ to $10^{-7}$ mm Hg for a period of between 6 and 24 hours have been found suitable. The support phase, under an inert atmosphere, suitably an atmosphere of dry nitrogen, or inert gas is then suspended in dry deoxygenated organic solvent, suitably a reaction inert hydrocarbon solvent such as toluene, slurried, and an excess suitably a 5% or greater excess of the desired zirconium tetralkyl, suitably tetraallyylzirconium or tetraneopentyl zirconium are added thereto. The mixture is slurried for from about 30 minutes to about 1 hour, the solvent separated by filtration and the residue dried under reduced pressure (suitably $10^{-5}$ mm Hg for three hours).

The thus produced product is then hydrogenated, suitably there is applied an excess suitably a 100 to 1,000% excess of hydrogen.

It has been found convenient to arrange the size of the vessel containing the material to be hydrogenated so that the applied pressure of hydrogen at ambient temperature is substantially below atmospheric pressure. The vessel is then, suitably, heated. It has been found convenient to carry out the hydrogenation in a temperature range of between 120° and 160° C. for about 30 minutes. The thus produced support-zirconyl dihydride 2 is then placed under an inert anhydrous atmosphere, suitably a dry nitrogen atmosphere and is ready for use.

The isomerization reaction is carried out in heterogeneous phase, either solid/gas or solid/gas/liquid. In the preferred embodiment the catalyst is slurried in a solvent, suitably a reaction inert anhydrous organic solvent, suitably a hydrocarbon solvent, preferably an aromatic hydrocarbon solvent such as toluene or the like. Olefin is then added to the slurry and, suitably, the closed vessel containing all components is agitated. The ratio of olefin to catalyst is not critical. It has been found that a ratio of 20 moles of olefin to 1 mole of catalyst is operative.

Larger amounts of catalyst will serve to increase the completion time of the isomerization whereas smaller amounts will tend to decrease the time of completion. The isomerization is carried out at ambient temperatures or slightly above ambient temperatures. In the case of certain complex, especially cyclic olefins higher temperatures, suitably in the range of 150°–200° C. may be desirable to achieve satisfactory reaction rates. For straight chain and branch chain olefins it has been found that a satisfactory rate of isomerization occurs at ambient temperature that is to say between about 15 and about 25 degrees while where cyclic moieties are involved, for example the isomerization of allylbenzene to the corresponding ω-methyl styrene temperatures about 20 to 30 degrees higher that is to say of the order of 45 to 65 degrees C. are preferred. The foregoing temperature readings should not be considered as limiting.

The mixture of isomers provided as a result of the foregoing procedure are then, if desired, separated into their components by methods well known in the art suitably by fractional distillation, preparation scale gas liquid chromatography and the like.

While the foregoing disclosure speaks of isomerization occurring in a closed system that is to say on a batch basis, the invention is in no way limited thereto. Isomerization may be carried out on a continual flow basis or, under suitable conditions, the thermodynamic equilibrium may be directed by the removal and/or recycling of certain components during the course of isomerization. Such methods include fractional distillation and the like which are well known to those skilled in the art.

EXPERIMENTAL

EXAMPLE I

Preparation of silica-$\mu,\mu$-dioxyzirconium dineopentyl

Silica (Aerosil brand, produced by Degussa) having a surface area of 300 m$^2$/g, (0.9 mM active OH/g) is heated under reduced pressure (200° C., $10^{-5}$ mmHg) for 12 hours.

A portion of said heat treated silica (200 mg) is charged to a sealable vessel containing dry toluene (10 ml, dried and deoxygenated by distillation from sodium and benzophenone). To this slurry is added an excess of zirconiumtetraalkyl (0.1 mM, quantities: alkyl=neopentyl, 50 mg; alkyl=allyl, 35 mg). No color change in the slurry is noted. The slurry is agitated for 35 minutes, and filtered through a glass sinter to yield the desired dialkyl silica-$\mu,\mu$-dioxyzirconium diallyl on the sinter.

Deposition of the product yields 2 moles of alkane per mole of zirconium as measured by vapor phase chromotographic analysis and by calibrated manometer.

EXAMPLE II

Preparation of silica-$\mu,\mu$-dioxyzirconium dihydride

The product of the foregoing example is transferred to 100 ml flask, and subjected to reduced pressure at ambient temperature ($10^{-5}$ mmHg) for three hours. To the same vessel hydrogen is then charged (1.1 mM hydrogen, 200 mmHg). The flask is then sealed and heated, under agitation for 30 minutes in an oil bath (temperature range of bath 120° to 160° C.).

Analysis of the gas phase of the reaction flask shows the formation of 2 moles of alkane per mole of zirconium, as measured by vapor phase chromatographic analysis and by calibrated monometer. I.R.: 1620 and 2190 cm$^{-1}$ (silica pellets, bridging and terminal zirconium hydride species).

In accordance with the above procedure but where in place of silica there is utilized as the carrier phase, alumina, zinc oxide, magnesia, calcium oxide, strontium oxide, barium oxide, titania, zirconia, vanadia, or boria there are obtained the corresponding metal oxide zirconium dihydrides.

EXAMPLE III

Isomerization of 1-butene with silica-$\mu,\mu$-dioxyzirconium dihydride (0.1 mM zirconium on silica (200 mg) is charged to a toluene (10 ml) added thereto. 1-butene (116 mg, 2.0 mM) is added and the mixture agitated. The progress of the reaction is monitored by vapor phase chromatographic analysis of the gas phase above the solution or by analysis of the liquid phase by similar methods. The reaction proceeds at 20° C. for 2 hours. The solid phase is then separated from the gas and liquid phase and the components separated by a fractional distillation to yield the corresponding isomers.

The composition of the isomerization product is set forth in table 1 below.

In accordance with the above procedures but omitting the use of toluene as a solvent, the isomerization reaction occurs to substantially the same extent at the same rate.

In accordance with the above procedure but where, in place of 1-butene there is isomerized 1-hexene[6] the isomerization is complete in 18 hours. The ratio of the components obtained is set forth in Table 1 below.

In accordance with the above procedure but where in place of 1-butene there is isomerized allylbenzene,[7] the reaction is carried out at 55° C. and is complete in 18 hours. The components obtained are set forth in Table 1 below.

In accordance with the above procedure with respect to allylbenzene but utilizing in place thereof methylenecyclohexane[8] the isomerization is substantially complete in about 5 days. The components obtained are set forth in Table 1 below.

In accordance with the above procedure but where, in place of methylenecyclohexane, there is utilized 5-vinyl bicyclo [2.2.1] heptene or propenyl bicyclo [2.2.1] heptene there is obtained 5-ethylidene bicyclo [2.2.1] heptene[9] and 5-propylidine bicyclo [2.2.1] heptene.

EXAMPLE IV

Analysis of catalyst after isomerization

After an isomerization run with 1-butene in toluene, the catalyst is filtered, dried under reduced pressure ($10^{-5}$ mmHg) and hydrolyzed with dilute sulphuric acid (2 N). A sample catalyst containing 0.27 mM of zirconium on 600 mg of silica is hydrolyzed with 15 ml of acid. Chromatographic analysis of the product indicates the formation of 1 mole of alkane per mole of zirconium. Formation of hydrogen is also detected but is not quantified.

These results show the formation of hydrogen silica-$\mu,\mu$,-dioxyzirconium alkyl hydride during the course of the isomerization procedure.

We claim:

1. A process for the isomerization of olefins selected from the group consisting of monounsaturated olefins and polyunsaturated olefins containing at least one non-conjugated double bond which comprises contacting said olefin in a substantially anhydrous, oxygen-free environment, with a catalyst of the formula

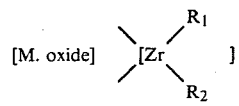

wherein [M-oxide] is a support phase selected from the group of oxides of group II, group III, group IV, group V and group VI B metals, silica, and germania, $R_1$ and $R_2$ are hydrogen or alkyl and may be the same or different.

2. A process of claim 1 wherein the alkyl moiety contains at least one hydrogen atom beta to the zirconium atom.

3. A process of claim 1 wherein [M-oxide] is selected from the group consisting of zinc oxide, magnesia, calcium oxide, strontium oxide, barium oxide, titania, zirconia, vanadia, boria, alumina, and silica.

4. A process according to claim 1 wherein [M.-oxide] is alumina or silica.

5. A process according to claim 1 wherein the [M.-oxide] component comprises two or more of the oxides of claim 1.

6. A process of claim 1 wherein the olefin is selected from the group consisting of:
a straight chain olefin of at least 4 carbon atoms,
a branched chain olefin of at least 5 carbon atoms,
a cycloalkene of at least 4 carbon atoms in the ring,
a polycycloalkene of at least 4 carbon atoms in each cycloalkene ring, where said cycloalkene rings may be fused to each other to provide a fused ring system or linked to each other by one or more carbon bonds to provide a polycycloalkene system having discrete ring moieties therein,
a cyclopolyalkene of at least 6 carbon atoms in the ring,
a polycyclopolyalkene of at least 6 carbon atoms wherein the rings of said system may be fused to each other or may be connected by one or more carbon carbon bonds to provide a polycyclic system having discrete ring moieties having at least one substituent in the ring,
alkenylcycloalkanes having at least 4 carbon atoms in the ring,

TABLE I

Relative Rates of Isomerization of Olefins by 2

| Starting Olefin | Product Olefin | Ratio of Product | Temp. (°C.) | Relative Rate[a] | Total Conversion[b] |
|---|---|---|---|---|---|
| 1-butene (5) | 1-butene | 1 | 20 | 50 | 2 h |
| | Cis-2-butene | 7 | | | |
| | trans-3-butene | 25 | | | |
| 1-hexene (6) | 1-hexene | 1 | 20 | 9 | 18 h |
| | Cis-2-hexene | 11.4 | | | |
| | trans-2-hexene | 40.9 | | | |
| | cis,trans-3-hexene | 15.6 | | | |
| allylbenzene (7) | allylbenzene | 3.6 | 55 | 9 | 18 h |
| | cis methylstyre | 1 | | | |
| | trans methyl-styrene | 14.3 | | | |
| Methylenecyclo-hexane (8) | 1-methyl cyclohexene | 5.0 | 55 | 1 | ≃5 days |
| | methylene cyclohexane | 1.0 | | | |
| | 3-methyl cyclohexene | | | | |
| | 4-methyl cyclohexene | | | | |

[a]Based on rate of initial turnover (at the indicated temperature)
[b]20 turnovers alkenylpolycycloalkanes having at least 4 carbon atoms in the ring wherein the ring systems may be fused to each other or connected by one or more carbon carbon bonds to provide polycyclic system having discrete ring moieties, alkenylcarbocyclicaromatic compounds wherein said alkenyl group has at least 3 carbon atoms, said aromatic groups selected from the group consisting of groups having a monocyclic aromatic nucleus, a monocyclicaromatic nucleus fused to at least 1 other aromatic nucleus, or bonded to another aromatic system by at least one carbon carbon linkage or a cyclic aromatic nucleus fused to an alicyclic moiety or bonded thereto by a carbon carbon bond.

7. A process for the isomerization of olefins selected from the group consisting of monounsaturated olefins and polyunsaturated olefins containing at least one nonconjugated double bond which comprises contacting said olefin in a substantially anhydrous, oxygen-free environment, at a temperature between ambient temperature and 200° C., with a catalyst of the formula

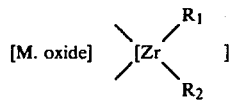

wherein [M-oxide] is a support phase selected from the group of oxides of group II, group III, group IV, group V and group VI B metals, silica, and germania, $R_1$ and $R_2$ are hydrogen or alkyl and may be the same or different.

* * * * *